United States Patent [19]

Weissman

[11] Patent Number: 5,385,469
[45] Date of Patent: Jan. 31, 1995

[54] METHOD FOR FORMING A CORONAL REPLACEMENT FOR A TOOTH AND PRODUCT FOR CASTING THE CROWN

[76] Inventor: Bernard Weissman, 225 E. 48th St., New York, N.Y. 10170

[21] Appl. No.: 56,696

[22] Filed: Apr. 30, 1993

Related U.S. Application Data

[63] Continuation-in-part of Ser. No. 898,769, Jun. 12, 1992, Pat. No. 5,326,263, and Ser. No. 976,606, Nov. 16, 1992, abandoned.

[51] Int. Cl.6 .......................... A61C 9/00; A61C 5/10
[52] U.S. Cl. ......................................... 433/40; 433/223
[58] Field of Search .................................. 433/40, 223

[56] References Cited

U.S. PATENT DOCUMENTS

| | | | |
|---|---|---|---|
| 1,893,520 | 1/1933 | Jaques | 433/223 |
| 1,902,850 | 3/1933 | Greene | 433/40 |
| 3,530,585 | 9/1970 | Goldstine | 433/40 |
| 3,686,754 | 8/1972 | Kondoloff | 433/223 |
| 4,144,645 | 3/1979 | Marshall | 433/223 |
| 4,255,140 | 3/1981 | Marshall | 433/40 |
| 4,362,508 | 12/1982 | Soderstrom | 433/40 X |
| 4,424,034 | 1/1984 | Korwin et al. | 433/40 |
| 4,483,675 | 11/1984 | Marshall | 433/40 X |
| 4,775,319 | 10/1988 | Knapp | 433/40 |
| 4,778,386 | 10/1988 | Spiry | 433/40 X |

*Primary Examiner*—Gene Mancene
*Assistant Examiner*—Nicholas D. Lucchesi
*Attorney, Agent, or Firm*—Barry G. Magidoff; Paul J. Sutton

[57] ABSTRACT

The invention provides a tubular dental mold form with at least one scalloped end and a method, utilizing the form, for forming a universal crown in situ on a tooth stump. In a preferred form, scalloped edges, of different depths, are formed at both ends and are circumferentially offset on one end with respect to the other end.

3 Claims, 4 Drawing Sheets

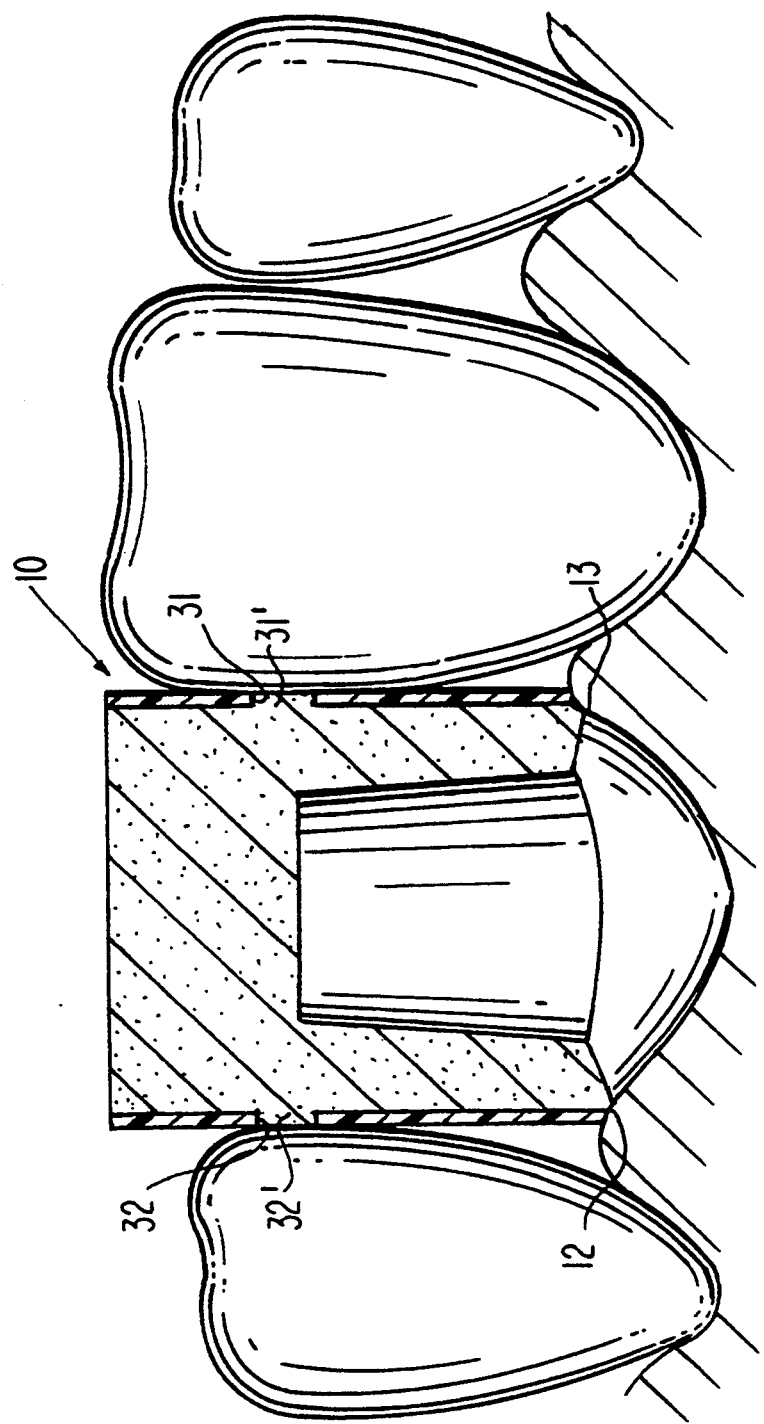

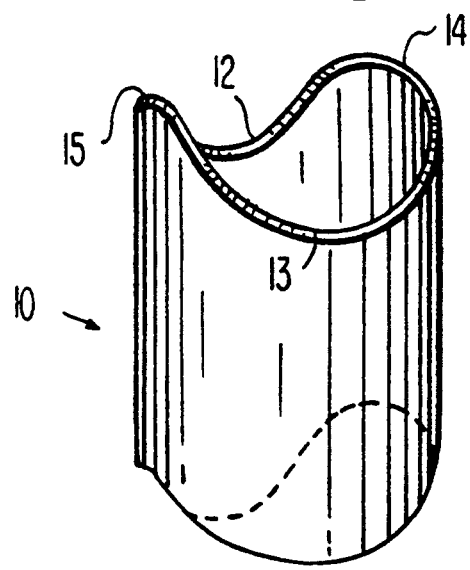
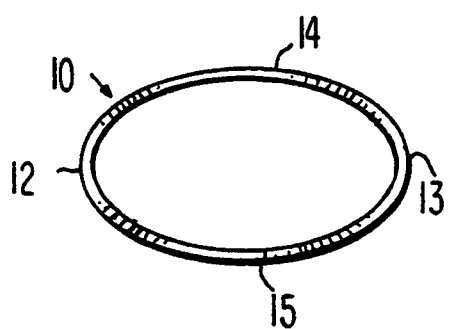
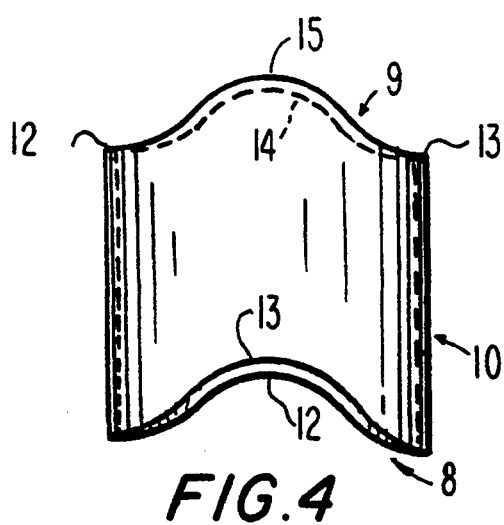
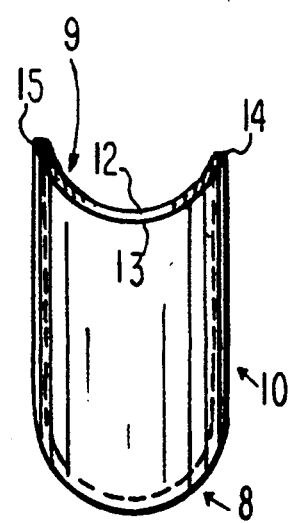

FIG.6
FIG.7
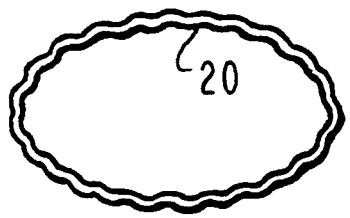
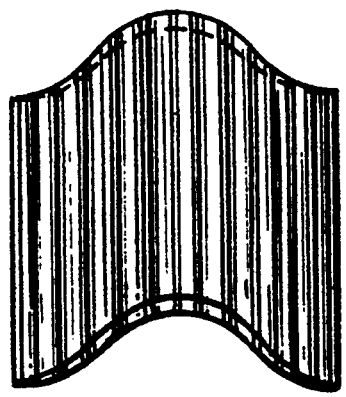
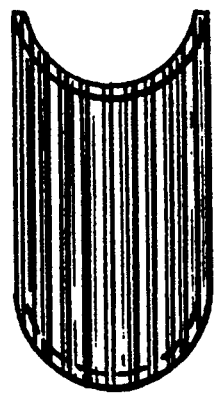
FIG.8          FIG.9

METHOD FOR FORMING A CORONAL REPLACEMENT FOR A TOOTH AND PRODUCT FOR CASTING THE CROWN

This application is a continuation in part of copending application Ser. No. 07/898,769, filed Jun. 12, 1992, now U.S. Pat. No. 5,326,263 and of No. 07/976,606, filed Nov. 16, 1992, now abandoned.

This application is directed to a method for forming a universal crown and a universal mold form for casting such a crown in situ on a tooth stump. It is not an uncommon problem met with by dental practitioners where the crown of a tooth has been broken in whole or in part, and a replacement must be quickly provided to prevent further damage to the tooth. Such situations may also involve the need to remove the nerve, and fully bore out the nerve canal.

Temporary crowns have generally been formed by applying various materials, e.g., curable composites, in small portions, to gradually build up the crown surface above the cleaned tooth stub, e.g., after a root canal operation. This has taken a great deal of time and can only be accomplished with great difficulty, even when a dental post was present to support the temporary crown, as shown, for example in the copending applications. In the past it has also been attempted to apply a tube, having one closed end and filled with composite, over the end of a tooth stub. When an upper tooth was being worked on, the closed tube was inverted; this also was not found to be wholly satisfactory because of the need to invert the tube, and further because such tubes did not fit closely around the base of the tooth, adjacent the gum, without causing damage to or tearing of the gingiva attachment.

It is an object of the present invention to provide a simple and efficient means of forming a temporary crown on a tooth stub, especially after the stub has been treated to remove the nerve from the canal, to quickly and straightforwardly obtain a compressed and condensed temporary crown pending completion of the permanent crown composite.

In accordance with the present invention, there is provided a dental mold form of a generally tubular shape, wherein at least one end of the form has a double scallop shape, wherein one scallop is more deeply indented than the opposing scallop. Preferably, the tube is formed of a material which will maintain its shape and most preferably is formed with an oval cross section.

The scalloped end has a generally sinusoidal form, having two convex curved portions and two concave curved portions. One of the concave portions is indented at least about 0.015 inches, and most preferably at least about 0.02 inches greater in depth. Most preferably the second end of the hollow tube is also scalloped, with the concave portions and convex portions being 90 degrees out of phase with the scallops on the opposite end of the tube. The scalloped tube is approximately at least about 9 millimeters in length and preferably not more than about 15 millimeters in length.

In accordance with the method of this invention, the tube is placed around a prepared tooth stub. In the case of a fully broken off tooth stub, where the coronal part has been fully removed, the nerve canal is cleared of any remaining nerve tissue. The tubular mold form is then placed around the tooth, so as to fit tightly around the tooth at least at the base of the tooth stub, i.e., at the portion immediately adjacent the gum line or gingiva. The scalloped end is so placed that the concave portions extend along the thickness of the tooth, and form an arc around the gum line. Curable composite material is packed into the tube, above and around the tooth, so as to be pressed tightly against, and in intimate contact with the remaining tooth substructure. After the composite has cured, the form is removed and the cured remaining crown material can then be formed by grinding with commonly available dental tools to the desired size and shape for a temporary condensed crown.

This method and the use of the special tube form in accordance with this invention permits the relatively fast and easy formation of a crown formed of condensed material, such as dental composite, free of voids or porosities, where food particles, discolorants and bacteria could accumulate. Such a crown will provide an intimate and tight fit with the tooth stub and the adjacent teeth so as to form a highly efficient and inexpensively prepared temporary, or even a permanent, crown.

This invention provides an additional benefit when multiple adjacent teeth are being treated. In a further preferred embodiment of this invention, a slit can be formed on opposing sides of the tube form, in the portions located in the interdental area. When this is done, the material packed into the tube form can extrude through the wall of the tube, forming a contact with the adjacent teeth to prevent floating, and to maintain the position of the teeth. When several adjacent teeth are being treated to form crowns, the series of contact elements formed by the side extrusions through the tube wall slits, can be used to form a connecting, splinted structure for the multiple coronal restoration.

Further details of preferred examples of the present invention are shown in the accompanying drawings, by way of example and not by way of exclusion. Many portions of the invention, or the context therefor, are shown in schematic representation, where greater detail is unnecessary as it will be apparent or well-known to those skilled in the art. Referring to the accompanying drawings:

FIG. 1 is a stylized front elevation view of anterior teeth including a single broken front tooth, as a prepared stub surrounded by a scalloped tube form in accordance with the present invention;

FIG. 2 is an isometric elevation view of a preferred scalloped tube form in accordance with the present invention;

FIG. 3 is a top view of the tube form of FIG. 2;

FIG. 4 is a front elevation view of the tube form of FIG. 2;

FIG. 5 is a side elevation view of the tube form of FIG. 2;

FIG. 6 is an isometric view of an alternative embodiment of the present invention showing a tube form of corrugated material;

FIG. 7 is a front elevation view of the tube form of FIG. 6;

FIG. 8 is a top view of the tube form of FIG. 6;

FIG. 9 is a side elevation view of the tube form of FIG. 6; and

Figure 10:
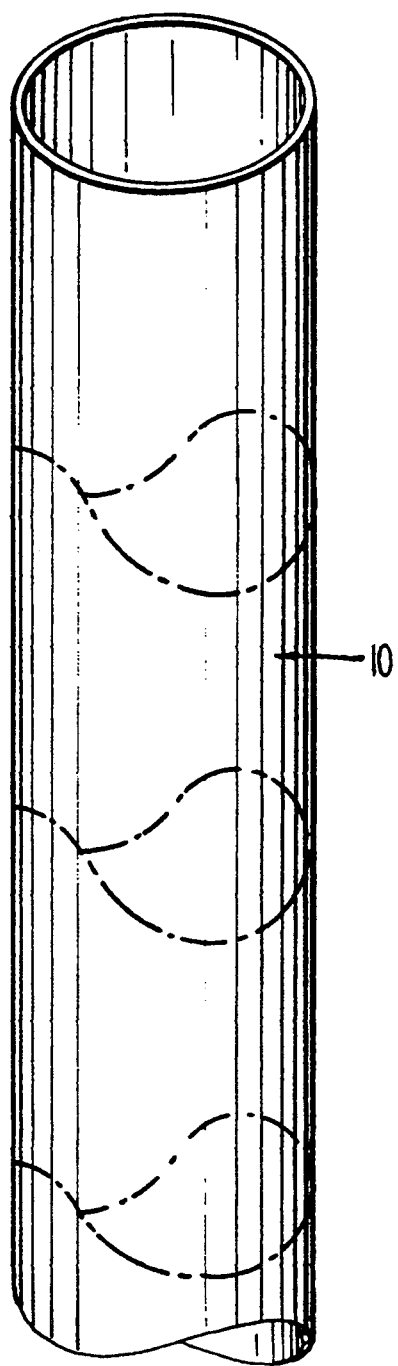
FIG. 10 is an isometric view of yet another embodiment of the present invention showing a portion of the method by which a scalloped tube form is manufactured.

Referring to the drawings, the preferred tube form of the present invention, generally indicated by the numeral 10 has an oval cross-section as shown in FIGS. 2 through 5. The size of each of the major and minor axes of the tube is determined by the width and thickness of the particular teeth for which the tube is to be used. For example, a tube having a major axis of 0.32 inches and a minor axis of 0.18 inches can be used for a stub of an upper anterior tooth, as is shown in FIG. 1. Generally, upper anterior teeth are less than 11 mm. in width; lower anterior teeth have a width of about 5 mm.; bicuspids have a width of from 6 to about 8 mm.; and molars have a width in the range of about 12 to about 16 mm.

The scalloped end portions 8,9, are shown as being 90 degrees out of phase, respectively; on each end are two unequal concave portions 12,13, one of which is at least of approximately 0.015 inches greater depth, and preferably not more than about 0.030 in, greater depth. In one most preferred embodiment, the offset between the two concave indents 12,13 are about 0.025 in. The convex portions 14,15 also vary by the same amounts, especially when the tube forms 10 are made by the preferred method. The scalloped ends permit tightly fitting the form tubes 10 over a tooth stub, when the orientation of the tube form relative to the tooth is such that the deeper concavity 13, is fitted over the higher portion of the gum, as shown in FIG. 1.

The tube form 10 of the present invention is preferably constructed of an intra-orally safe, light transmitting material, transparent or translucent, most preferably between 3 and 8 thousandths of an inch in thickness. Such materials are well known. In addition, these materials should also have a sufficiently high elasticity modulus such that at the desired wall thickness the tube form will hold its shape, but can be elastically deformed by finger pressure to accommodate the slightly different sizes and shapes of teeth. The wall thickness of the tube form is limited by the spacing between teeth such that a form can be placed over a tooth stub, and fit in the gap between the stub being crowned and the adjacent tooth.

In the tube form shown by FIGS. 6 through 9, the tube wall 20 is manufactured in corrugated form, so as to permit expansion to accommodate different size teeth, without actual stretching of the material. Such a corrugated tube form is otherwise formed of the same size and shape as the tube form disclosed by FIGS. 2-5.

The light transmitting wall material for the tube form permits the use of light curable composite for forming the crown. Alternatively, it is also included within the scope of this invention to utilize autopolymerizing resin, or other material which is cured by means other than the application of light, such as by the application of heat or water. In such cases, the tube form wall material need not be light transmissive.

Although the tube forms of the present invention can be formed having a circular cross-section, the oval tube cross-section shown in the drawings is preferred because it more closely matches the shape of teeth; in addition, the tube form can be placed on either the wider but less thick anterior teeth, or on the thicker, but less wide, bicuspids. The tube forms which have a scalloped edge at both ends, permit the placement of the proper concave indent at the interdental gum line, by turning the tube upside down, i.e., turning it 180 degrees about an axis perpendicular to the longitudinal axis of the tube, and rotating it 90 degrees about its longitudinal axis, so that the highest portion of the gum line engages the most deeply cut indent, or scallop 13. Thus, the alternate shallower and deeper scalloping of the tube ends, accommodate the range of differing natural gum curvatures and slopes found in the normal population.

The tube form 10 is placed around the tooth stub as shown in FIG. 1, and pushed tightly against the lower portion of the tooth stub to form a tight contact at the gum line. At the same time, the scalloped bottom ends prevent damage to the tooth gingiva attachments during the casting procedure. The dentist can then form, as with a scalpel, small openings 31,32 through the portion of the tube wall touching or opposite the adjacent teeth, to permit extrusion of a small amount of, e.g., the curable composite material 31',32' therethrough; when hardened, this extruded material provides a contact with the adjacent teeth to prevent floating, or movement, of the teeth.

The end of the tube form extending beyond the tooth line can be trimmed, or shortened, and pressed together, before placing the crown material into the tube, to provide for the formation of a cast form more closely conforming to the intended final appearance or shape of the crown. After the crown material, or composite, has hardened or cured, the tube wall material can be removed by cutting and tearing away from the crown, thus leaving the extruded contact material 31', 32' in place. After the tube is removed, the cast shape can then be further formed by cutting away excess material, leaving a proper size temporary crown and one having the desirable intimate and tight contacts both with the stump being covered and with respect to adjacent teeth.

This form can also be used for forming the necessary mold when casting crowns, inlays or posts and cores by the direct technique, when accomplished in situ. The cured material can then be shaped to the desired form and sent to a laboratory for casting into the final metal material through, for example, the lost wax process. By so doing, the dentist avoids the need for taking costly impressions, making casts and having most of the process done by a dental laboratory. When the tubular forms are formed of material having a somewhat greater rigidity, they can be formed in several different sizes, to for example accommodate the upper anterior teeth, the lower anterior teeth, both upper and lower bicuspids and upper and lower molars. Alternatively, a single basic form size can be used for more than one of these teeth depending on the individual.

The material for forming the tube form preferably can be formed of the following orally safe materials: polypropylene, Teflon, and other safe polyolefins.

The tube forms of this invention can be manufactured by extruding a long tube of material having the desired cross-sectional size, as shown in FIG. 10, and cutting the tube to the desired length, and with the desired scalloped end edges.

The patentable embodiments of this invention which are claimed are as follows:

1. A dental mold form comprising a generally tubular outer wall having first and second opposing ends; a double scallop formed at each of the first and the second ends, comprising a first scallop and an opposing second scallop, one scallop at each end being more deeply indented than the opposing scallop at that end, the scallops at the second end being oriented circumferentially ninety degrees out of phase with the scallops at the first end; the tubular outer wall having a length of an order of magnitude equal to that of teeth, said length being approximately at least about nine millimeters and not more than about fifteen millimeters, and being formed of an orally safe material having a sufficient modulus of stiffness to retain its shape but to be deformable radially under finger pressure.

2. The dental mold form of claim 1, wherein the tube has substantially an oval cross section.

3. A method for forming a dental crown in situ, on a tooth stub having a broken portion, the method comprising cleaning the tooth stub to remove all diseased tissue, placing a tubular mold form in accordance with claim 1 around the stub and forming a tight fit around the base of the stub, below the broken portion, the scalloped end concave portion extending over the gum line at the interdental portion; packing curable composite material into the tube form; compressing the material through the open end of the tube form; curing the composite material; removing the tube form; mechanically forming the cured composite to the desired size and shape; and cutting a hole trough the tube form wall at a position between the tooth stub and adjacent teeth, so as to cause the composite to extrude therethough and form a contact with the adjacent teeth; and wherein the tube is removed from around the tooth stub after curing of the composite by cutting away from around the contact.

* * * * *